(12) United States Patent
Mpock

(10) Patent No.: US 7,939,030 B2
(45) Date of Patent: May 10, 2011

(54) MICRO MECHANICAL METHODS AND SYSTEMS FOR PERFORMING ASSAYS

(75) Inventor: Emmanuel C. Mpock, Salida, CA (US)

(73) Assignee: MEC Dynamics Corp., Salida, CA (US)

( * ) Notice: Subject to any disclaimer, the term of this patent is extended or adjusted under 35 U.S.C. 154(b) by 1149 days.

(21) Appl. No.: 10/976,651

(22) Filed: Oct. 29, 2004

(65) Prior Publication Data

US 2005/0136551 A1    Jun. 23, 2005

Related U.S. Application Data

(60) Provisional application No. 60/515,731, filed on Oct. 29, 2003.

(51) Int. Cl.
*G01N 33/00* (2006.01)

(52) U.S. Cl. ........ 422/402; 422/401; 422/407; 422/408; 422/412

(58) Field of Classification Search ............ 422/401, 422/402, 407, 408, 412; 436/177
See application file for complete search history.

(56) References Cited

U.S. PATENT DOCUMENTS

| | | | |
|---|---|---|---|
| 4,756,884 A | 7/1988 | Hillman et al. | |
| 4,868,129 A * | 9/1989 | Gibbons et al. | 436/179 |
| 5,173,433 A | 12/1992 | Bachand | |
| 5,541,117 A | 7/1996 | Karl et al. | |
| 5,686,316 A | 11/1997 | Fiechtner et al. | |
| 5,726,026 A | 3/1998 | Wilding et al. | |
| 5,744,096 A | 4/1998 | Jones et al. | |
| 6,136,610 A | 10/2000 | Polito et al. | |
| 6,372,513 B1 | 4/2002 | Nguyen et al. | |
| 6,555,389 B1 | 4/2003 | Ullman et al. | |
| 6,773,671 B1 | 8/2004 | Lewis et al. | |
| 6,780,651 B2 | 8/2004 | Douglas et al. | |
| 6,818,455 B2 | 11/2004 | May et al. | |
| 2002/0173044 A1 | 11/2002 | Pachl et al. | |

(Continued)

FOREIGN PATENT DOCUMENTS

DE    3618989 A1    12/1987

(Continued)

OTHER PUBLICATIONS

Australian Patent Office Examiner's First Report, Australian Patent Office Application No. 2004286284, Jan. 22, 2010, 2 pages.

(Continued)

*Primary Examiner* — Sam P Siefke
(74) *Attorney, Agent, or Firm* — Fenwick & West LLP

(57) ABSTRACT

The present invention provides a micro mechanical system for performing assays for determining the presence of one or more selected analytes in a sample. The device comprises of a base and a disposable strip with at least one reaction well and at least one moveable member capable of moving fluids and parts through the fluids in a defined reaction well. Reagents in the reaction chambers and or the moveable members, react with the sample to yield a physically detectable change. The moveable parts are capable of executing motions that either mix, move reaction components, exchange or systematically deliver reagents to targets in the cartridge. Sensors in the base are configured to detect and or quantify the presence of a sample in the reaction well and of analytes in the sample. The signal is converted to an output on a visual display window on the external part of the base.

15 Claims, 3 Drawing Sheets

U.S. PATENT DOCUMENTS

| | | |
|---|---|---|
| 2003/0003522 A1 | 1/2003 | Goldman |
| 2003/0073243 A1 | 4/2003 | Law et al. |
| 2003/0153094 A1 | 8/2003 | Alocilja et al. |
| 2004/0115831 A1 | 6/2004 | Meathrel et al. |
| 2004/0121450 A1 | 6/2004 | Pugia et al. |
| 2004/0156037 A1 | 8/2004 | Mawhirt et al. |
| 2004/0184954 A1 | 9/2004 | Guo et al. |
| 2004/0191124 A1 | 9/2004 | Noetzel et al. |
| 2004/0214345 A1 | 10/2004 | Matzinger et al. |

FOREIGN PATENT DOCUMENTS

| | | |
|---|---|---|
| EP | 1120164 A2 | 8/2001 |
| EP | 1195607 A2 | 4/2002 |
| FR | 2721112 | 6/1994 |
| JP | 09-072904 | 3/1997 |
| JP | 09-262084 | 10/1997 |
| JP | 2790359 | 6/1998 |
| JP | 2002-501173 | 1/2002 |
| JP | 2003-503731 | 1/2003 |
| JP | 2004-223115 | 8/2004 |
| WO | WO 00/42430 | 7/2000 |
| WO | WO 01/28683 A1 | 4/2001 |
| WO | WO 01/63299 A1 | 8/2001 |
| WO | WO 03/083479 A1 | 10/2003 |
| WO | WO 2004/042364 A2 | 5/2004 |
| WO | WO 2004/065010 A2 | 8/2004 |

OTHER PUBLICATIONS

European Patent Office Supplementary Search Report, European Patent Application No. EP 04796769, Sep. 3, 2009, 4 pages.

Japanese Patent Office Office Action, Japanese Application No. 2006-538319, Nov. 19, 2009, 7 pages.

Letter from Bufete Soni re Mexican Institute of Industrial Property Office Action, Mexican Patent Application No. 06/04810, Mar. 26, 2009, 1 page.

Letter from Bufete Soni re Mexican Institute of Industrial Property Office Action, Mexican Patent Application No. 06/04810, Aug. 18, 2009, 5 pages.

Patent Office of the Russian Federation, Russian Patent Application No. 2006118365, Sep. 2, 2008, 5 pages.

State Intellectual Property Office of the People's Republic of China, PRC Patent Application No. 200480035145.X, Oct. 9, 2009, 13 pages.

European Patent Office Examination Report, European Patent Application No. EP 04 796 769.0, Sep. 10, 2010, six pages.

Indian Patent Office First Examination Report, Indian Patent Application No. 1147/KOLN/2006, May 31, 2010, three pages.

PCT International Search Report and Written Opinion, PCT/US04/36031, Mar. 5, 2008, 8 pages.

* cited by examiner

MICRO MECHANICAL METHODS AND SYSTEMS FOR PERFORMING ASSAYS

RELATED APPLICATION DATA

This application claims the benefit of U.S. provisional patent application No. 60/515,731 filed on Oct. 29, 2003, which is herein incorporated by reference in its entirety.

FIELD OF INVENTION

The present invention relates to microfluidics systems for performing assays for determining the presence of one or more selected analytes in a sample.

BACKGROUND

Qualitative and quantitative immuno- and chemical assays have gained acceptance as important tools in the medical and food industries. These methods have been used for the diagnosis of disease conditions, detection of analytes, and for the detection of microbes, such as bacteria. These methods of diagnosis have established effectiveness, and the methods have made it easier for physicians to monitor and manage patients undergoing various forms of therapy.

Traditionally, the diagnostic assays have been performed in hospital and clinic settings, and involve the use of sophisticated and expensive equipment, that require specially trained personnel for their operation. Further, the assay results are sometimes not available for days or weeks after the samples from the patients have been obtained. The presently available diagnostic assays are thus costly, time consuming, and not convenient.

Attempts have been made to develop less costly assays. For example, a typical home self-test for detecting blood components requires the patient to prick a finger with a sterilized lancet, apply a drop of blood sample to a sample application area on the disposable strip, and then wait for the results. Assays that use other bodily fluids, such as urine essentially work in a similar manner. These devices are designed such that a typical lay person can perform the assays correctly with very little training. However, these assay systems generally suffer from low accuracy or require a number of preparative steps be performed that could compromise the test results, and are thus not convenient.

U.S. Pat. No. 5,580,794 to Allen Michael describes a single use electronic assay device that assays for specific analytes in a given sample. U.S. Pat. No. 4,806,312 to Greenquist describes a multizone analytical element having detectable signal concentration zone. U.S. Pat. No. 4,627,445 to Garcia et al. describes a hand-held portable medical diagnostic system for checking measurement of blood glucose, urea nitrogen, hemoglobin, or blood components, where a disposable needle or lance probe package carries a chemical reagent strip such as blood reacting chemistry, a visual readout, and a computer system.

U.S. Pat. No. 4,197,734 to A. Rosenberg describes an apparatus that is capable of measuring the clotting time of blood. The apparatus includes a support frame, which supports a syringe containing a blood sample, and a turntable that rotates. Blood from the syringe drops onto the turntable where the clotting time is automatically and graphically depicted by a chart that is rotated on the turntable. The apparatus can also be employed to determine variations in the viscosity of blood plasma and other fluids.

U.S. Pat. No. 3,486,859 to Greiner et al. describes an apparatus that has a double arm holder with blood liquid reactant chambers that are connected to each other via a small capillary conduit. An air pump is provided for applying pressure changes to one of the chambers to effect periodic mixing of the liquids via the capillary conduit. Indicator means are included to detect the progressive restriction of the capillary conduit upon coagulation of the blood.

The methods described above have severe limitations which make them extremely challenging for home use. Some of the methods require special blood preparations and handling, making them suitable for a central clinic with well-trained staff, while others are expensive, or not accurate. Thus, there is a need for assay systems for detecting analytes that are accurate, convenient, and inexpensive.

SUMMARY

The present invention provides methods and micro technological systems for performing assays for determining the presence of one or more preselected analytes in a sample. The apparatus includes a disposable plastic strip that can be inserted into a portable handheld test analysis machine. The strip isolates the sample such that it is not in contact with the machine and the sample is not contaminated.

The disposable strip of the present invention can have a plurality of defined wells on a solid support. The wells can be linked by capillary channel. The surface of the wells and the capillary channels can be coated with reagents to assist in drawing the liquid sample from the sample well into the reaction wells. Inside at least one of the reaction chambers is at least one magnetic stir bar which can be attracted magnetically and driven by a magnetic moving device arranged outside the strip in the test analysis machine. The magnetic stir bar is capable of executing motions that mix the reaction components, move reaction components, exchange or systematically deliver reagents to targets in the cartridge, and the like.

The strip can be placed on a portable handheld machine having sensors configured to detect and or quantify the presence of an analyte in the reaction wells of the strip, while responding to the physically detectable changes, producing signals which correlate to the presence of and or amount of the selected analyte in the sample. The reagents can comprise the detection system, whereby a detectable result occurs in relation to the presence of an analyte. The signal can be converted to an output on a visual display window on the external part of the base.

To test a sample, the disposable strip can be inserted into the base, and the sample drop can be placed in the sample application well of the strip. The sample can be drawn into the reaction well through the internal channels. As the sample is drawn into the reaction wells, sensors detect the movement and activate the magnetic stir bar at the appropriate times which mix the reagents within the sample well. For timed assays, a microprocessor contained within the base begins a time count while the sensors, which can be electrical or optical, monitor various parts of the strip for specific analyte responses. When detected and or quantified, the results are reported qualitatively or quantitatively with the appropriate units in the display window on the base.

The motion and the sensors can be microprocessor controlled. A heater assembly can be activated in the base, for temperature-sensitive assays such as coagulation tests and the temperature can be held constant or varied in a predetermined way through the duration of the assay.

In one aspect of the invention, a disposable strip is described where the disposable strip comprises a first solid substrate comprising a sample collection well, a reference well, and a reaction well, wherein the wells are in fluidic communication via a first capillary channels; and a second solid substrate comprising holes wherein the first solid substrate and the second solid substrate are joined and the holes communicate with the wells.

In another aspect of the invention, a disposable strip comprising a first solid substrate comprising a sample application well, a reference well, and a reaction well, wherein the wells are in fluidic communication via capillary channels, and wherein the reference well comprises a first lysing agent and the reaction well comprises a second lysing agent, an antibody, and a stir bar; a second solid substrate comprising holes wherein the first solid substrate and the second solid substrate are joined and the holes communicate with the wells; and a membrane having a capture zone wherein the membrane is connected to the reaction well via a second capillary channel is described.

In yet another aspect, the invention pertains to a method for determining the percentage of hemoglobin that is HbA1c, the method comprising providing a disposable strip comprising a first solid substrate comprising a sample well, a reference well, and a reaction well, wherein the wells are in fluidic communication via a first capillary channel, and wherein the reference well comprises a first lysing agent and the reaction well comprises a second lysing agent, a HbA1c specific antibody, and a stir bar; a second solid substrate comprising holes wherein the first solid substrate and the second solid substrate are joined and the holes communicate with the wells; and a membrane having a capture zone wherein the membrane is connected to the reaction well via a second capillary channel; placing a sample in the sample application well; adding a diluent to the sample application well; determining the total hemoglobin from the reference cell and the total HbA1c from the capture zone; and dividing the total HbA1c by total hemoglobin to obtain the percentage of hemoglobin that is HbA1c.

These and other aspects of the present invention will become evident upon reference to the following detailed description. In addition, various references are set forth herein which describe in more detail certain procedures or compositions, and are therefore incorporated by reference in their entirety.

DETAILED DESCRIPTION

I. Definitions

Figure 1:
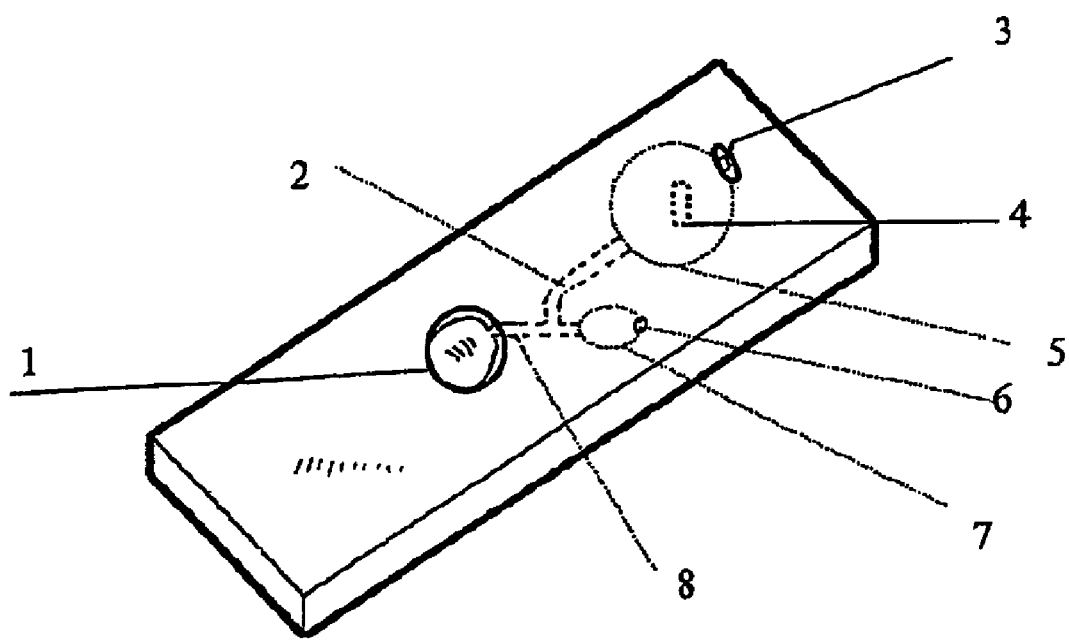
FIG. 1 illustrates a perspective view of the disposable strip with a set of interconnected reaction chambers and a moveable member in one of the chambers.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise.

All publications, patents and patent applications cited herein, whether supra or infra, are hereby incorporated by reference in their entirety.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

The term "antibody," as used herein, includes, but is not limited to a polypeptide substantially encoded by an immunoglobulin gene or immunoglobulin genes, or fragments thereof which specifically bind and recognize an analyte (antigen). "Antibody" also includes, but is not limited to, a polypeptide substantially encoded by an immunoglobulin gene or immunoglobulin genes, or fragments thereof which specifically bind and recognize the antigen-specific binding region (idiotype) of antibodies produced by the host in response to exposure to trichomonas antigen(s). Examples include polyclonal, monoclonal, chimeric, humanized, and single chain antibodies, and the like. Fragments of immunoglobulins, include Fab fragments and fragments produced by an expression library, including phage display. See, e.g., Paul, Fundamental Immunology, $3^{rd}$ Ed., 1993, Raven Press, New York, for antibody structure and terminology.

The terms "specifically binds to" or "specifically immunoreactive with" refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular antigen. For example, solid-phase ELISA immunoassays are routinely used to select monoclonal antibodies specifically immunoreactive with an analyte. See Harlow and Lane (1988) Antibodies, A Laboratory Manual, Cold Spring Harbor Publications, New York, for a description of immunoassay formats and conditions that can be used to determine specific immunoreactivity. Typically a specific or selective reaction will provide a signal to noise ratio at least twice background and more typically more than 10 to 100 times background.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like.

As used herein, a "solid support" refers to a solid surface such as a plastic plate, magnetic bead, latex bead, microtiter plate well, glass plate, nylon, agarose, acrylamide, and the like.

"Specific" in reference to the binding of two molecules or a molecule and a complex of molecules refers to the specific recognition of one for the other and the formation of a stable complex as compared to substantially less recognition of other molecules and the lack of formation of stable complexes with such other molecules. Exemplary of specific binding are antibody-antigen interactions, enzyme-substrate interactions, polynucleotide hybridizations and/or formation of duplexes, cellular receptor-ligand interactions, and so forth.

II. Overview

The invention pertains to a disposable strip that can be used for performing qualitative and quantitative immuno- and chemical assays. On the strip are at least three wells, where the wells can be in fluidic communication with each other via capillary channels. In one well is placed the sample, preferably a liquid sample, for analysis. The sample fluid moves into the other two wells via the capillary channels. One of the wells can serve as a standard that measures the total analyte in the sample. The other well can serve as the reaction well, where individual components of the sample can be identified. The disposable strip can be placed in an analyzer (also referred to herein as a "base") that detects the individual components of the sample and the total analyte in the sample. The analyzer includes a display system that can display the results of the analysis as well as provided instructions during the operation of the assay.

In one application, the percent total hemoglobin that is hemoglobin A1c (HbA1c) in human red blood cell can be determined. Blood from a subject can be deposited in the sample well. The blood is moved into the other two wells via the capillary channels. In the reference well can be placed a reagent that lyses the cells thereby releasing the hemoglobin from the red blood cells. The concentration of hemoglobin in the reference cell can be measured using infrared or ultraviolet measurements. In the reaction well can be placed a lysate, a known amount of an antibody specific for HbA1c, and a magnetic stirrer. When blood moves into the reaction well, the magnet stirs the liquids in the well thereby mixing them well. The lysate lyses the cells, and the antibody binds to HbA1c. After a specified period of time, the display can instruct the operator to add a diluent to the reaction well. The diluent pushes the liquid in the reaction chamber through another capillary channel towards one or more capture zones. The capture zones have immobilized on them antigens that bind to the bound antibody complex only, and on a separate part of the zone other antigens that bind to all antibodies. The antibody-HbA1c complex can be captured by the antigens in the first part of the capture zone, and all the antibodies can be captured by the antigens in the latter part of the capture zone. A detection system can be used to detect the antibodies bound in the first and the second part of the capture zone. The ratio and/or the sum of the two zones can be used to quantify the amount of HbA1c present in the sample. The ratio of the first zone to the total hemoglobin from the reference cell can provide the percentage of HbA1c in the blood sample. The results can be displayed on the display system

III. Micro Mechanical System

The invention provides a disposable strip, a portable handheld machine (i.e., a base), and a combination comprising a disposable strip and a base. The strip can be placed on the machine for performing assays, for detecting analytes, and for displaying information such as instructions and results. One aspect of the disposable strip is illustrated in FIG. 1. The disposable strip can be made by joining together two or more solid supports with grooves present in at least one of the supports. The solid support can be rectangular, circular, oval, or any shape. The support can be made from a suitable material that is selected on its properties, such as good thermal conductivity, clarity for optical transmission, mechanical properties for easy welding, surface properties that allow for uniform coating and stability of reagent, and neutrality to the liquid medium to prevent interference with the assay. For this purpose, suitable plastics include those with high free surface energies and low water sorption, including PETG, polyester (Mylar®), polycarbonate (Lexan®), polyvinyl chloride, polystyrene, SAN, acrylonitrile-butadiene-styrene (ABS), particularly ABS supplied by Borg Warner under the trade name Cycolac, among others. When the solid support is a hydrophobic plastic, it can be treated by art-known methods to render the surfaces hydrophilic, such as by plasma etching and by corona treatment. Alternatively and equivalently, a commercially-available molded solid support can be used in the practice of the invention.

For purposes of illustration, this embodiment of the invention is described by reference to a disposable strip formed by joining two solid supports. At least one of the solid supports has grooves or cavities that serve as the reaction chambers 5 and 7, and capillary channels 2 and 8. The grooves can be any geometric shape, and are preferably circular. The grooves have dimensions that are sufficient volume to hold the samples and to allow for the reaction to occur. Thus, the circular grooves can have a diameter of between about 0.01 mm to about 100 mm, depending on the length and width of the support material, and can have a height of about 0.001 mm to about 4 mm, depending on the thickness of the support material. The diameter and height of the grooves can be easily determined by the one of skill in the art. In one aspect of the invention, one of the support pieces has holes drilled through to the grooves where the holes serve as the vent holes 3 and 6. Further, the holes can allow access to the well where the sample will be placed, such as the sample application well, 1. Prior to the joining of the two pieces, the moveable member, 4, can be inserted in the desired reaction chamber, 5.

In the molding process, energy-directing ridges are needed at least on the outline adjacent to the periphery of the groove of at least one of the two plastic pieces. When welded ultrasonically, the two plastic pieces are glued together along the energy ridges forming an air-tight seal around the chambers and channels, with the only access to the exterior from the reaction chambers being the vent holes and sample application well. The surface of the reaction chamber can optionally be slightly textured for use with moveable members. The texturing can accommodate a disjoining pressure, Π. Π, is the pressure, in the case of two plates immersed in a medium, in excess of the external pressure, that must be applied to the medium between the plates to maintain a given separation. In this case, Π is numerically just the force of attraction or repulsion between the moveable member and the surfaces of the reaction chamber per unit area. The wider the moveable member, the greater would be the pressure between the surfaces and texturing would eliminate any undesired clamping of the moveable member unto the walls of the reaction chamber. A more general definition for disjoining pressure is $$\Pi = -1/\check{A}(\delta G/\delta x) \; \check{A}, \; T, \; V \text{ where}$$

Ǎ=Area
T=Temperature
V=Volume
G=Gibb's free energy

The moveable member, 4, can be made by use of stainless steel or a combination of stainless steel with any other desired material so that it is capable of being attracted and driven by an external magnetic moving device. The material can be any form of magnetizable alloy with a stainless covering to prevent corrosion or specially coated for bonding of specific molecules. The thickness of the movable member is based on the height of the reaction chamber. It has to be small enough to fit in the reaction chamber and move freely. For a reaction chamber cavity of a height of 0.010 inches, the thickness of the moveable member can be between about 0.007 to about 0.008 inches.

The mode for applying the sample to the reaction chambers as well as other reagents, such as salt and sugar solutions to the capillary channels include spraying, painting, lyophilization, evaporation, adsorption, covalent conjugation or the like. For reagents with large particulate components, spray painting or lyophilization would be adequate. Biodeposition of pico liter drop sizes results in instantaneous drying when dispensed at room temperature due to the size of the drops.

Figure 2:
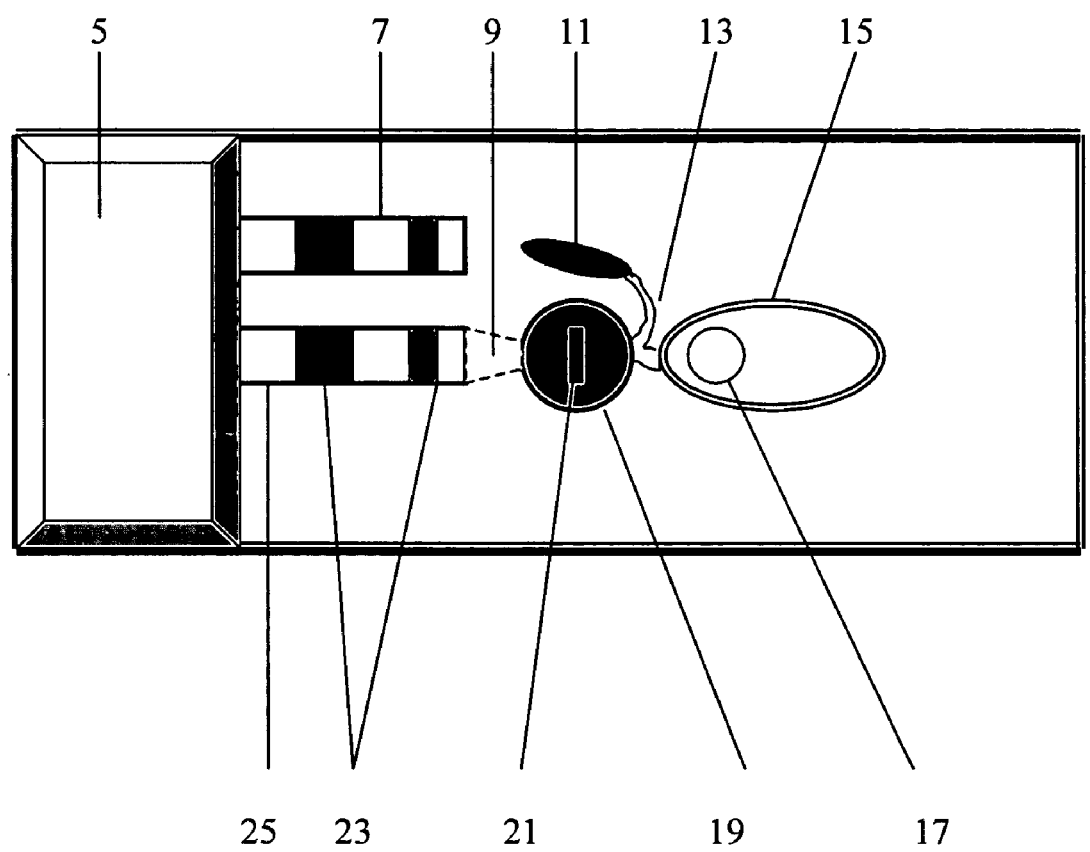
FIG. 2 illustrates another view of the disposable strip comprising a composite of membranes assembled to isolate the blood components and directing the desired analyte to the proper capture zones.

An assembled disposable strip is illustrated in FIG. 2, where 5 is an absorbent pad, 7 is an internal reference membrane strip, 9 is a capillary channel, 11 is a reaction chamber, 13 is a capillary channel, 15 is a sample receptacle, 17 is a sample application port, 19 is a reaction chamber, 21 is a moveable member, 23 are capture zones on a base membrane 25.

Figure 3:
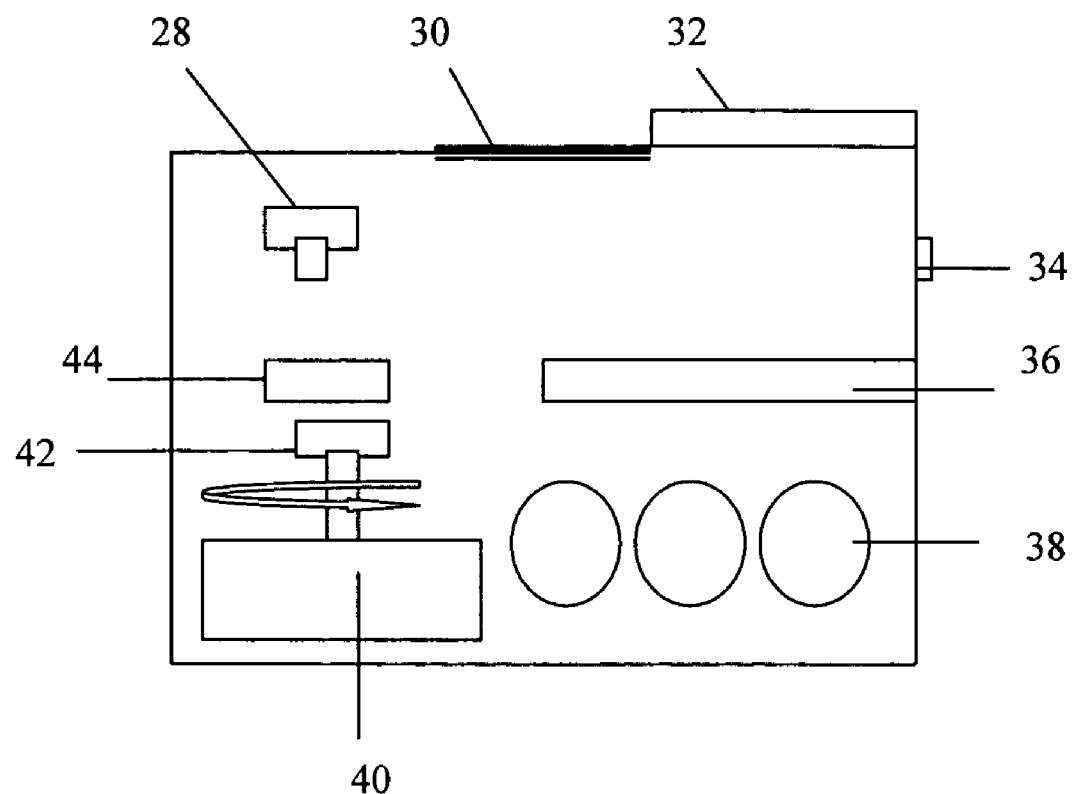
FIG. 3 illustrates a perspective view of the main components in the base device as described in detail below.

FIG. 3 is a perspective diagram of the main components of the analyzer into which the disposable strip is inserted prior to applying a test sample. The disposable strip can be positioned at 46 on the base. The strip can be placed on top of a heater assembly 44 that may accommodate a sensor (emitters and or detectors) embedded in it or in close proximity but arranged such that a signal goes through the reaction chamber. Another set of sensors that also can serve as emitters, detectors, or both can be positioned on the other side of the disposable strip (not shown). It is to be understood that the reflective beam arrangement, the detector and the emitter can be on the same side of the strip, depending on the detection mechanism that is used. The detection mechanism is not limited to an optical detection method, but other methods, such as electrical, radioactive, and other methods could also be used. An electronic display window 30 can be, but is not limited to, a Liquid Crystal Display, LCD. 28, represents switches or keys on a membrane for function selection from a menu displayed on the LCD. The electronic board 36 comprises a microprocessor that controls the operation and mechanics of the analyzer. The power can be supplied by batteries 38, or any other source of alternate electrical power supply. The motor 40 drives the magnet, 42, and the two can be connected, such as by a rod. The defined motion pattern of the motor and magnet are responsible for creating the corresponding motion of the moveable member in one or more of the reaction chambers of the disposable strip. 32, represents a connector to an external power supply and 34 represents a connector for data output.

An example of a detection system for automated detection for use with the present disposable strip and associated methods comprises an excitation source, a monochromator (or any device capable of spectrally resolving light components, or a set of narrow band filters) and a detector array. The excitation source can comprise infrared, blue or UV wavelengths and the excitation wavelength can be shorter than the emission wavelength(s) to be detected. The detection system may be: a broadband UV light source, such as a deuterium lamp with a filter in front; the output of a white light source such as a xenon lamp or a deuterium lamp after passing through a monochromator to extract out the desired wavelengths; or any of a number of continuous wave (cw) gas lasers, including but not limited to any of the Argon Ion laser lines (457, 488, 514, etc. nm) or a HeCd laser; solid-state diode lasers in the blue such as GaN and GaAs (doubled) based lasers or the doubled or tripled output of YAG or YLF based lasers; or any of the pulsed lasers with output in the blue.

The emitted light from the sample or the reactants in the reaction well can be detected with a device that provides spectral information for the substrate, e.g., a grating spectrometer, prism spectrometer, imaging spectrometer, or the like, or use of interference (bandpass) filters. Using a two-dimensional area imager such as a CCD camera, many objects may be imaged simultaneously. Spectral information can be generated by collecting more than one image via different bandpass, longpass, or shortpass filters (interference filters, or electronically tunable filters are appropriate). More than one imager may be used to gather data simultaneously through dedicated filters, or the filter may be changed in front of a single imager. Imaging based systems, like the Biometric Imaging system, scan a surface to find fluorescent signals.

Other embodiments appropriate for this system include the use of reagent-coated membranes systems as part of the strip positioned in a way that allows continuity and directed sample flow within the entire strip system. The sensory systems would be positioned to be capable of monitoring the membrane portions of the strip for the analyte or responses being tested for.

IV. Operation

A general mode of operation of the device shown in FIG. 3 involves the insertion of the disposable strip shown in FIGS. 1 and 2 into a receptacle that allows the strip on one position only. For an assay with a specific temperature requirement, the heater assembly, 44, heats the disposable strip to the desired temperature controlled by the microprocessor. The LCD prompts simple steps, after the strip is inserted and the analyzer turned on, which the operator can follow including the addition of the sample to the sample receptacle. The instrument can optionally have sensors to determine the presence of adequate amounts of sample in the reaction chambers and a mechanism to initiate and stop the timing of the assay. The sensor detect the signals from the completion of the reaction, such as measuring the transmission of an optical signal emitted and directed through the walls of the reaction chamber.

The applied sample is accurately distributed into the various reaction chambers via the capillary channels. The positioning of the reaction chambers can be such that independent reactions can occur in the various reaction chambers even though they share a common sample from the same pool. The defined modes of movement of the moveable member ensures proper mixing of the reagent and sample mixtures and also contributes in inter chamber reagent and sample interchange. For assays that require quantification of an analyte, the sensory system monitors the changes either in one or more reaction chambers, a membrane system or the moveable members, until the desired end point is achieved. For assays requiring just the determination of the presence of an analyte, the sensory system monitors the specific parts of the strip for the appropriate duration of time. The microprocessor computes the results quantitatively or qualitatively, which are displayed on the LCD. The strip can then be removed at the end of the assay and disposed.

Thus, the operator inserts the strip into strip receptacle in the analyzer. The operator then pushes a start button, which could automatically be activated by the strip itself, waits for a prompt to add a drop of sample, and then obtains the results from the display, typically within a few minutes or seconds, depending on the assay type.

V. Detection of Hemoglobin A1c (HbA1c)

Glycated hemoglobin refers to a series of minor hemoglobin components that are formed through the attachment of glucose to the hemoglobin molecule. The human red blood cell is freely permeable to glucose. Within each red blood cell, glycated hemoglobin is formed at a rate that is directly proportional to the ambient glucose concentration. Approximately 97% of the total hemoglobin in circulating red blood cells is hemoglobin A. Hemoglobin A consists of four polypeptide chains, two a-chains and two b-chains. Glycation of the Hemoglobin A occurs through the covalent coupling of glucose with the N-terminal valine amino acid of each b-peptide chain. An unstable Schiff base (aldimine) is initially formed which then undergoes an irreversible Amadori rearrangement to form a stable ketoamine, Hemoglobin A1c (HbA1c).

The life-span of hemoglobin A containing red blood cells averages 120 days. The percentage of Hemoglobin A that is glycated to HbA1c is directly proportional to the time that red blood cells are exposed to glucose and to the average glucose concentration encountered. Measurement of the HbA1c fraction gives an integrated picture of the average blood glucose concentration during the half-life of the red cells, that is, over the last 60 days. The level of HbA1c is usually expressed as a percentage of total hemoglobin.

In normal subjects, HbA1c is typically in the range 3-6% of total hemoglobin. In patients with elevated glucose levels e.g. in the case of Type I and Type 2 diabetes, the level may rise to twice the upper limit of normal or more.

Long-term control of glucose levels in diabetics is very important. Too much glucose in the blood over many years can damage the eyes, kidneys and nerves. It also increases the risk for heart and blood vessel disease. The measurement of HbA1c as a percentage of total hemoglobin provides a valuable means of assessing the long-term control of glucose levels and also constitutes an important risk indicator for identifying Type 1 and Type 2 diabetics.

A sample of blood from a subject can be obtained in deposited in the sample well 15 of the disposable strip (FIG. 2). The blood moves to the reaction chambers 11 and 19 via the capillary channels 13. The reaction chamber 11 can serve as the reference where the total hemoglobin is measured. The reaction chamber 19 measures the HbA1c in the blood sample. The ratio of HbA1c to the total hemoglobin provides the percentage of total hemoglobin that is HbA1c.

Both of the reaction chambers contain a lysing agent. The lysing agent lyses the whole blood samples thereby releasing the hemoglobin. The lysing agents are typically surfactants, and preferably nonionic surfactants, such as for example TRITON™ X-100. The reaction chamber 19 additionally contains an antibody that can detect HbA1c. The antibody can be a monoclonal or polyclonal antibody (Ab), or Ab fragment containing the antigen binding site, or complementarity determining region (CDR), such as an F(ab')$_2$ or Fab fragment. The detectable moiety or label may be a radioactive, fluorescent or chemiluminescent substance, or an enzyme. Alternatively, a labeled-second Ab which recognizes the species specific Fc fragment of the first Ab may also be used. Further, the antibody may be labeled with a detectable label.

In one aspect, the detectable label is a fluorescent molecule. Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester), rhodamine (5,6-tetramethyl rhodamine), substituted rhodamine compounds, and the cyanine dyes Cy3, Cy3.5, Cy5, Cy5.5 and Cy7. The absorption and emission maxima, respectively, for these fluorophores are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent lablels can be obtained from a variety of commercial sources, including Molecular Probes, Eugene, OR and Research Organics, Cleveland Ohio. As another alternative, in place of an added label, the bound hemoglobin itself, sue to its peroxidase-like properties, can generate a detectable signal. This is accomplished by adding hydrogen peroxide, with or without addition of another substrate (e.g. isoluminol).

The cells in the two reaction wells are lysed. In the reference well 11, the total amount of hemoglobin can be obtained by spectroscopic methods, such as measuring in the UV region or the infrared region. The spectroscopic apparatus is known in the art and is incorporated within the portable handheld machine. In particular, the measurements can be made at 880 nm and at 580 nm. In the reaction well 19, the antibodies bind to HbA1c. In order to ensure complete reaction, the liquids in the reaction wells can be magnetically stirred, and optionally heated to a higher temperature.

Upon completion of the reaction, a diluent can be added to the sample well 15. The diluent causes the reactants in 19 to move through the capillary channels 9 towards the capture zones 23. The capture zones can be antigens or other compounds that can specifically bind to the antibody-HbA1c complex, any antibody, and the like or combinations thereof. Thus, in one aspect, the first capture zone contains antigens that specifically bind to the antibody-HbA1c complex, while the second capture zone contains antigens that bind to the antibody and the antibody-HbA1c complex. The absorbent pad 5 absorbs all the liquid and can help in drawing the liquid from the wells through the membranes.

The amount of material in each capture zone can be determined by using the detection systems described above. Calibrators or standards that are run with the assay provide calibration (or standard) curves from which the % HbA1c in the sample is determined using the measured signal. The sum of all the capture zones preferably equals the amount of antibody that was placed in the reaction well, and can provide an internal control to determining the percentage of reaction that has occurred. The concentration of the antibody-HbA1c complex can be determined from the reading of the first capture zone. The % HbA1c in the blood sample can be determined by dividing the concentration of the antibody-HbA1c complex with the total concentration of hemoglobin.

In another aspect, a reference membrane 7 (FIG. 2) can be included in the disposable strip. The reference membrane can have deposited upon it known concentrations of the antigen-antibody-HbA1c complex, and antigen-antibody complex. The spectrophotometric measurements form the reference membrane can be used to calibrate the readings from the active membrane 25.

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

I claim:

1. A disposable strip comprising:
   a first solid substrate comprising a sample collection well, a reference well, and a reaction well, wherein the wells are in fluidic communication via a first capillary channel, and wherein the reference well and the reaction well comprise a lysing agent;
   a second solid substrate comprising holes wherein the first solid substrate and the second solid substrate are joined and the holes communicate with the wells; and
   a membrane having a capture zone wherein the membrane is connected to the reaction well via a second capillary channel.

2. The disposable strip of claim 1, wherein the first substrate and the second substrate are rectangular.

3. The disposable strip of claim 1, wherein the substrate is selected from the group consisting of plastic, glass, nylon, metal, and combinations thereof.

4. The disposable strip of claim 3, wherein the substrate is plastic.

5. The disposable strip of claim 1, further comprising a stir bar in the reaction well.

6. The disposable strip of claim 1, further comprising an antibody deposited in the reaction well.

7. The disposable strip of claim 6, wherein the antibody is specific for HbA1c.

8. The disposable strip of claim 1, wherein the lysing agent is a nonionic surfactant.

9. The disposable strip of claim 1, wherein the membrane is interposed between an absorbent pad and the reaction well.

10. The disposable strip of claim 1, wherein the substrate is selected from the group consisting of plastic, glass, nylon, metal, and combinations thereof.

11. The disposable strip of claim 10, wherein the substrate is plastic.

12. A disposable strip comprising:
   a first solid substrate comprising a sample application well, a reference well, and a reaction well, wherein the wells are in fluidic communication via capillary channels, and wherein the reference well comprises a first lysing agent and the reaction well comprises a second lysing agent, an antibody, and a stir bar;
   a second solid substrate comprising holes wherein the first solid substrate and the second solid substrate are joined and the holes communicate with the wells; and
   a membrane having a capture zone wherein the membrane is connected to the reaction well via a second capillary channel.

13. The disposable strip of claim 12, wherein the first substrate and the second substrate are rectangular.

14. The disposable strip of claim 12, wherein the first and the second lysing agents are nonionic surfactant.

15. The disposable strip of claim 12, wherein the antibody is specific for HbA1c.

* * * * *